United States Patent
Frank et al.

(10) Patent No.: US 8,386,034 B2
(45) Date of Patent: Feb. 26, 2013

(54) DEFIBRILLATOR WITH UTILITY LIGHT

(75) Inventors: Mark Frank, Dresden (DE); Jil Cruz, Issaquah, WA (US); Micha Coleman, Woodinville, WA (US); Benjamin A. Flugstad, Port Ludlow, WA (US); Fred W. Chapman, Renton, WA (US)

(73) Assignee: Physio-Control, Inc., Redmond, WA (US)

( * ) Notice: Subject to any disclaimer, the term of this patent is extended or adjusted under 35 U.S.C. 154(b) by 0 days.

(21) Appl. No.: 13/087,229

(22) Filed: Apr. 14, 2011

(65) Prior Publication Data

US 2012/0071940 A1    Mar. 22, 2012

Related U.S. Application Data

(60) Provisional application No. 61/385,499, filed on Sep. 22, 2010.

(51) Int. Cl.
*A61N 1/39* (2006.01)

(52) U.S. Cl. .............. 607/5; 607/2; 607/9; 607/115; 320/107

(58) Field of Classification Search .............. 607/5
See application file for complete search history.

(56) References Cited

U.S. PATENT DOCUMENTS

| | | | | |
|---|---|---|---|---|
| 5,906,426 A | * | 5/1999 | Farrington et al. | 362/198 |
| 7,272,441 B1 | * | 9/2007 | Chapman et al. | 607/5 |
| 7,618,153 B2 | * | 11/2009 | O'Hern | 362/197 |
| 7,810,964 B2 | * | 10/2010 | Probasco | 362/372 |
| 8,036,742 B2 | * | 10/2011 | Sullivan et al. | 607/5 |
| 8,104,934 B2 | * | 1/2012 | Probasco | 362/428 |
| 2003/0026103 A1 | * | 2/2003 | Reese et al. | 362/486 |
| 2004/0133242 A1 | * | 7/2004 | Chapman et al. | 607/5 |
| 2006/0229680 A1 | * | 10/2006 | Chapman et al. | 607/5 |
| 2007/0247108 A1 | * | 10/2007 | Brown | 320/107 |
| 2010/0182780 A1 | * | 7/2010 | Hilt | 362/198 |
| 2010/0219775 A1 | * | 9/2010 | Maglica et al. | 315/362 |
| 2011/0058361 A1 | * | 3/2011 | Houghton | 362/184 |

* cited by examiner

*Primary Examiner* — Carl H Layno
*Assistant Examiner* — Michael Carey
(74) *Attorney, Agent, or Firm* — Marger Johnson & McCollom, P.C.

(57) ABSTRACT

Embodiments of the present concept are directed to external defibrillators that include a utility light for use by one or more rescuers using the defibrillator. In one implementation, an external defibrillator has a housing, an energy storage module for storing an electrical charge, a defibrillation port for guiding the stored electrical charge to a person, and a processor for determining when to guide the electrical charge. The defibrillator also includes a user interface that includes a screen showing indications by light, and a separate utility light coupled to the housing via a light-coupling structure. The utility light is structured to generate and cast a beam of light with a beam divergence angle of no more than 160 degrees in order to illuminate a certain point of the local environment. This illumination capability may help rescuers reach a person in need of medical attention and apply medical assistance to the person.

30 Claims, 8 Drawing Sheets

DEFIBRILLATOR WITH UTILITY LIGHT

FIG. 1  *DEFIBRILLATION SCENE*

| TYPE OF EXTERNAL DEFIBRILLATOR | INTENDED TO BE USED BY PERSONS: ||
|---|---|---|
| | IN THE MEDICAL PROFESSIONS | NOT IN THE MEDICAL PROFESSIONS |
| DEFIBRILLATOR – MONITOR | √ | |
| AED | √ | √ |

FIG. 2  *TWO MAIN TYPES OF EXTERNAL DEFIBRILLATORS*

FIG. 3

COMPONENTS OF EXTERNAL DEFIBRILLATOR

*DEFIBRILLATOR WITH UTILITY LIGHT*

FIG. 4

FIG. 5  *DEFIBRILLATOR WITH FIXED UTILITY LIGHT*

FIG. 6  *DEFIBRILLATOR WITH POSITIONABLE UTILITY LIGHT MOUNTING SYSTEM*

FIG. 7  *DEFIBRILLATOR WITH UTILITY LIGHT*

FIG. 8  *DEFIBRILLATOR WITH DETACHABLE UTILITY LIGHT*

FIG. 9  *DEFIBRILLATOR WITH UTILITY LIGHT*

FIG. 10 *DEFIBRILLATOR WITH UTILITY LIGHT*

FIG. 11 — METHOD OF ILLUMINATING CERTAIN POINT OF RESCUE ENVIRONMENT

DEFIBRILLATOR WITH UTILITY LIGHT

CROSS REFERENCE TO RELATED PATENT APPLICATIONS

This patent application claims priority from U.S. Provisional Patent Application Ser. No. 61/385,499, filed on Sep. 22, 2010, the disclosure of which is hereby incorporated by reference for all purposes.

FIELD

This invention generally relates to external defibrillators.

BACKGROUND

In humans, the heart beats to sustain life. In normal operation, it pumps blood through the various parts of the body. More particularly, the various chamber of the heart contract and expand in a periodic and coordinated fashion, which causes the blood to be pumped regularly. More specifically, the right atrium sends deoxygenated blood into the right ventricle. The right ventricle pumps the blood to the lungs, where it becomes oxygenated, and from where it returns to the left atrium. The left atrium pumps the oxygenated blood to the left ventricle. The left ventricle, then, expels the blood, forcing it to circulate to the various parts of the body.

The heart chambers pump because of the heart's electrical control system. More particularly, the sinoatrial (SA) node generates an electrical impulse, which generates further electrical signals. These further signals cause the above-described contractions of the various chambers in the heart, in the correct sequence. The electrical pattern created by the sinoatrial (SA) node is called a sinus rhythm.

Sometimes, however, the electrical control system of the heart malfunctions, which can cause the heart to beat irregularly, or not at all. The cardiac rhythm is then generally called an arrhythmia. Arrhythmias may be caused by electrical activity from locations in the heart other than the SA node. Some types of arrhythmia may result in inadequate blood flow, thus reducing the amount of blood pumped to the various parts of the body. Some arrhythmias may even result in a Sudden Cardiac Arrest (SCA). In a SCA, the heart fails to pump blood effectively, and, if not treated, death can occur. In fact, it is estimated that SCA results in more than 250,000 deaths per year in the United States alone. Further, a SCA may result from a condition other than an arrhythmia.

One type of arrhythmia associated with SCA is known as Ventricular Fibrillation (VF). VF is a type of malfunction where the ventricles make rapid, uncoordinated movements, instead of the normal contractions. When that happens, the heart does not pump enough blood to deliver enough oxygen to the vital organs. The person's condition will deteriorate rapidly and, if not reversed in time, they will die soon, e.g. within ten minutes.

Ventricular Fibrillation can often be reversed using a life-saving device called a defibrillator. A defibrillator, if applied properly, can administer an electrical shock to the heart. The shock may terminate the VF, thus giving the heart the opportunity to resume pumping blood. If VF is not terminated, the shock may be repeated, often at escalating energies.

A challenge with defibrillation is that the electrical shock must be administered very soon after the onset of VF. There is not much time: the survival rate of persons suffering from VF decreases by about 10% for each minute the administration of a defibrillation shock is delayed. After about 10 minutes the rate of survival for SCA victims averages less than 2%.

The challenge of defibrillating early after the onset of VF is being met in a number of ways. First, for some people who are considered to be at a higher risk of VF or other heart arrythmias, an Implantable Cardioverter Defibrillator (ICD) can be implanted surgically. An ICD can monitor the person's heart, and administer an electrical shock as needed. As such, an ICD reduces the need to have the higher-risk person be monitored constantly by medical personnel.

Regardless, VF can occur unpredictably, even to a person who is not considered at risk. As such, VF can be experienced by many people who lack the benefit of ICD therapy. When VF occurs to a person who does not have an ICD, they collapse, because blood flow has stopped. They should receive therapy quickly.

For a VF victim without an ICD, a different type of defibrillator can be used, which is called an external defibrillator. External defibrillators have been made portable, so they can be brought to a potential VF victim quickly enough to revive them.

While some external defibrillators are used in environments with bright lighting, such as in a hospital, many environments where external defibrillators are used in rescue situations have poor lighting conditions. With low light conditions, navigating around the environment, and also possibly operation and use of the defibrillator and related implements can be difficult. Separate flashlights or headlights can be used in some situations, but require that the rescuer locate and bring another, separate device. Additionally, many separate flashlights require the use of one of the rescuer's hands for optimal operation, which makes certain rescue procedures difficult to perform because of the limited use of the hand holding the flashlight. Further, in some rescue situations, lighting conditions can be unknown or change unexpectedly.

BRIEF SUMMARY

The present description gives instances of medical devices, systems, and methods, the use of which may help overcome problems and limitations of the prior art.

In particular, embodiments of the present concept are directed to external defibrillators that include a utility light for use by one or more rescuers carrying, and also possibly using the defibrillator and related implements.

In some embodiments, an external defibrillator that is structured for use in a local environment with an ambient light level includes a housing having a light-coupling structure. An energy storage module is included in the housing for storing an electrical charge, and a defibrillation port is used for guiding the stored electrical charge to a person via one or more electrodes coupled to the energy storage module. The external defibrillator also includes a processor for determining when to guide the electrical charge and a user interface that includes a screen showing indications by light. To illuminate a certain point of the local environment, the external defibrillator also includes a utility light distinct from the screen. The utility light is coupled to the housing by being received matingly with the light-coupling structure and structured to generate and cast a beam of light at the certain point with a beam divergence angle of no more than 160 degrees.

In other embodiments, a method is disclosed to illuminate a certain point of a rescue environment. The method includes bringing a defibrillator that stores an electrical charge within a rescue environment. The defibrillator includes a screen showing indications by light, a light-coupling structure, and a utility light matingly received with the light-coupling structure and distinct from the screen. The method also includes activating a switch to provide power to the utility light so as to generate a beam of light with a beam divergence angle of no more than 160 degrees and directing the utility light so as to cast the beam towards a certain point of the environment. If it is otherwise indicated by the defibrillator, the method also includes using the defibrillator to deliver the charge to treat a patient in the environment.

An advantage over the prior art is that the utility light of the external defibrillator can provide a rescuer with the ability to illuminate certain points of a rescue environment without having to rely on a separate lighting device that can be forgotten or difficult to operate in a rescue situation. In addition, the utility light of the defibrillator may be controlled to provide communications to a rescuer or other user.

These and other features and advantages of this description will become more readily apparent from the following Detailed Description, which proceeds with reference to the drawings, in which:

BRIEF DESCRIPTION OF THE DRAWINGS

FIG. 2 is a table listing two main types of the external defibrillator shown in FIG. 1, and who they might be used by.

DETAILED DESCRIPTION

As has been mentioned, the present description is about medical devices, systems, and methods for illuminating a rescue environment with a utility light connected to an external defibrillator.

Embodiments are now described in more detail.

Figure 1:
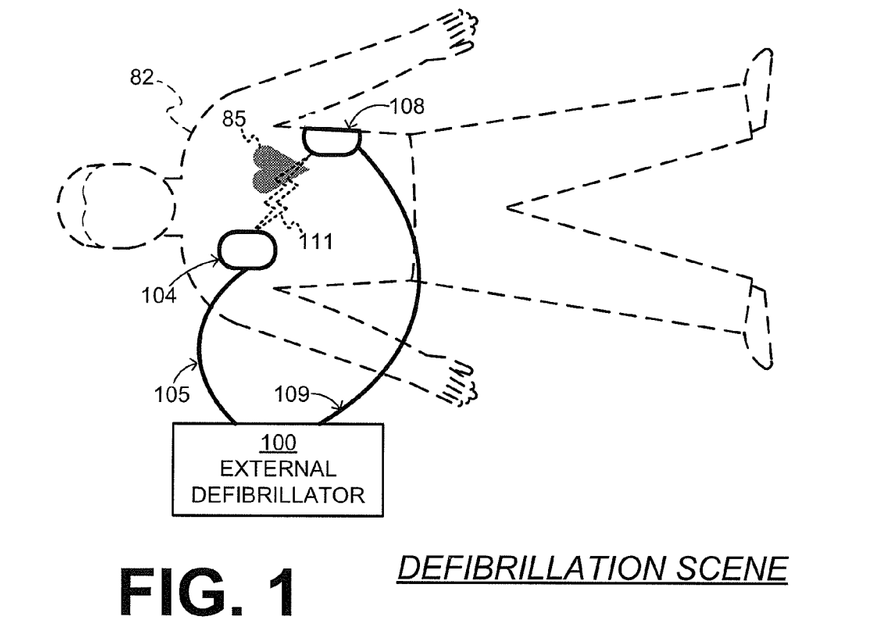
FIG. 1 is a diagram of a scene where an external defibrillator is used to save the life of a person according to embodiments.

FIG. 1 is a diagram of a defibrillation scene. A person 82 is lying on their back. Person 82 could be a patient in a hospital, or someone found unconscious, and then turned to be on their back. Person 82 is experiencing a condition in their heart 85, which could be Ventricular Fibrillation (VF).

A portable external defibrillator 100 has been brought close to person 82. At least two defibrillation electrodes 104, 108 are usually provided with external defibrillator 100, and are sometimes called electrodes 104, 108. Electrodes 104, 108 are coupled with external defibrillator 100 via respective electrode leads 105, 109. A rescuer (not shown) has attached electrodes 104, 108 to the skin of person 82. Defibrillator 100 is administering, via electrodes 104, 108, a brief, strong electric pulse 111 through the body of person 82. Pulse 111, also known as a defibrillation shock, goes also through heart 85, in an attempt to restart it, for saving the life of person 82.

Defibrillator 100 can be one of different types, each with different sets of features and capabilities. The set of capabilities of defibrillator 100 is determined by planning who would use it, and what training they would be likely to have. Examples are now described.

Figure 2:
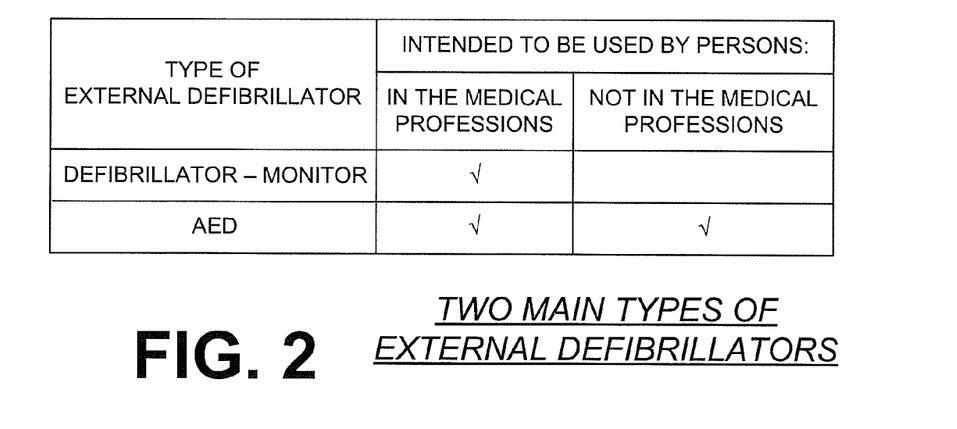

FIG. 2 is a table listing two main types of external defibrillators, and who they are primarily intended to be used by. A first type of defibrillator 100 is generally called a defibrillator-monitor, because it is typically formed as a single unit in combination with a patient monitor. A defibrillator-monitor is sometimes called monitor-defibrillator. A defibrillator-monitor is intended to be used by persons in the medical professions, such as doctors, nurses, paramedics, emergency medical technicians, etc. Such a defibrillator-monitor is intended to be used in a pre-hospital or hospital scenario.

As a defibrillator, the device can be one of different varieties, or even versatile enough to be able to switch among different modes that individually correspond to the varieties. One variety is that of an automated defibrillator, which can determine whether a shock is needed and, if so, charge to a predetermined energy level and instruct the user to administer the shock. Another variety is that of a manual defibrillator, where the user determines the need and controls administering the shock.

As a patient monitor, the device has features additional to what is minimally needed for mere operation as a defibrillator. These features can be for monitoring physiological indicators of a person in an emergency scenario. These physiological indicators are typically monitored as signals. For example, these signals can include a person's full ECG (electrocardiogram) signals, or impedance between two electrodes. Additionally, these signals can be about the person's temperature, non-invasive blood pressure (NIBP), arterial oxygen saturation/pulse oximetry (SpO2), the concentration or partial pressure of carbon dioxide in the respiratory gases, which is also known as capnography, and so on. These signals can be further stored and/or transmitted as patient data.

A second type of external defibrillator 100 is generally called an AED, which stands for "Automated External Defibrillator". An AED typically makes the shock/no shock determination by itself, automatically. Indeed, it can sense enough physiological conditions of the person 82 via only the shown defibrillation electrodes 104, 108 of FIG. 1. In its present embodiments, an AED can either administer the shock automatically, or instruct the user to do so, e.g. by pushing a button. Being of a much simpler construction, an AED typically costs much less than a defibrillator-monitor. As such, it makes sense for a hospital, for example, to deploy AEDs at its various floors, in case the more expensive defibrillator-monitor is more critically being deployed at an Intensive Care Unit, and so on.

AEDs, however, can also be used by people who are not in the medical profession. More particularly, an AED can be used by many professional first responders, such as policemen, firemen, etc. Even a person with only first-aid training can use one. And AEDs increasingly can supply instructions to whoever is using them.

AEDs are thus particularly useful, because it is so critical to respond quickly, when a person suffers from VF. Indeed, the people who will first reach the VF sufferer may not be in the medical professions.

Increasing awareness has resulted in AEDs being deployed in public or semi-public spaces, so that even a member of the public can use one, if they have obtained first aid and CPR/

AED training on their own initiative. This way, defibrillation can be administered soon enough after the onset of VF, to hopefully be effective in rescuing the person.

There are additional types of external defibrillators, which are not listed in FIG. 2. For example, a hybrid defibrillator can have aspects of an AED, and also of a defibrillator-monitor. A usual such aspect is additional ECG monitoring capability.

Figure 3:
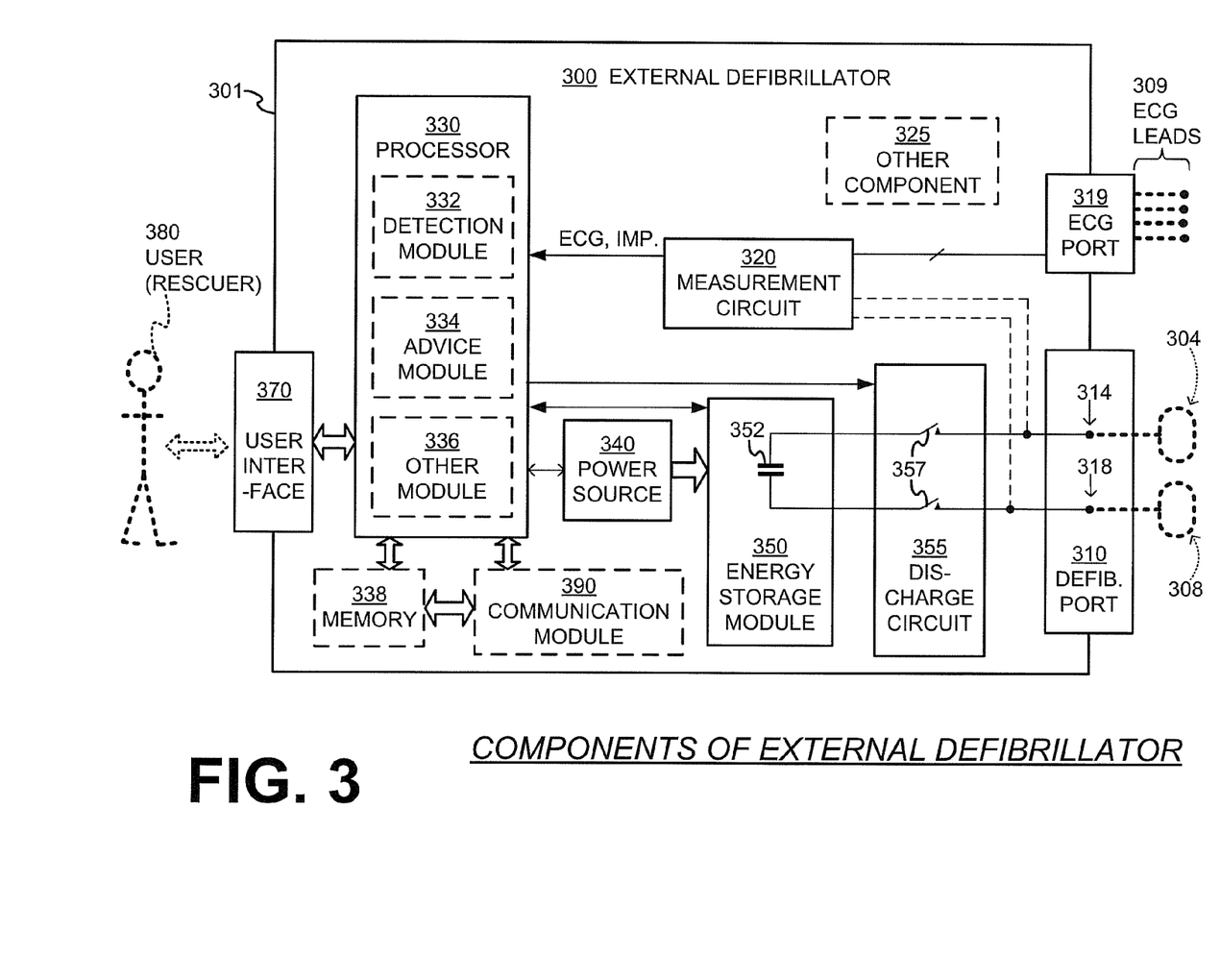
FIG. 3 is a diagram showing components of an external defibrillator, such as the one shown in FIG. 1, which is made according to embodiments.

FIG. 3 is a diagram showing components of an external defibrillator 300 made according to embodiments. These components can be, for example, in external defibrillator 100 of FIG. 1. Plus, these components of FIG. 3 can be provided in a housing 301, which is also known as casing 301.

External defibrillator 300 is intended for use by a user 380, who would be the rescuer. Defibrillator 300 typically includes a defibrillation port 310, such as a socket in housing 301. Defibrillation port 310 includes nodes 314, 318. Defibrillation electrodes 304, 308, which can be similar to electrodes 104, 108, can be plugged in defibrillation port 310, so as to make electrical contact with nodes 314, 318, respectively. It is also possible that electrodes can be connected continuously to defibrillation port 310, etc. Either way, defibrillation port 310 can be used for guiding via electrodes to person 82 an electrical charge that has been stored in defibrillator 300, as will be seen later in this document.

If defibrillator 300 is actually a defibrillator-monitor, as was described with reference to FIG. 2, then it will typically also have an ECG port 319 in housing 301, for plugging in ECG leads 309. ECG leads 309 can help sense an ECG signal, e.g. a 12-lead signal, or from a different number of leads. Moreover, a defibrillator-monitor could have additional ports (not shown), and an other component 325 for the above described additional features, such as patient signals.

Defibrillator 300 also includes a measurement circuit 320. Measurement circuit 320 receives physiological signals from ECG port 319, and also from other ports, if provided. These physiological signals are sensed, and information about them is rendered by circuit 320 as data, or other signals, etc.

If defibrillator 300 is actually an AED, it may lack ECG port 319. Measurement circuit 320 can obtain physiological signals through nodes 314, 318 instead, when defibrillation electrodes 304, 308 are attached to person 82. In these cases, a person's ECG signal can be sensed as a voltage difference between electrodes 304, 308. Plus, impedance between electrodes 304, 308 can be sensed for detecting, among other things, whether these electrodes 304, 308 have been inadvertently disconnected from the person.

Defibrillator 300 also includes a processor 330. Processor 330 may be implemented in any number of ways. Such ways include, by way of example and not of limitation, digital and/or analog processors such as microprocessors and digital-signal processors (DSPs); controllers such as microcontrollers; software running in a machine; programmable circuits such as Field Programmable Gate Arrays (FPGAs), Field-Programmable Analog Arrays (FPAAs), Programmable Logic Devices (PLDs), Application Specific Integrated Circuits (ASICs), any combination of one or more of these, and so on.

Processor 330 can be considered to have a number of modules. One such module can be a detection module 332, which senses outputs of measurement circuit 320. Detection module 332 can include a VF detector. Thus, the person's sensed ECG can be used to determine whether the person is experiencing VF.

Another such module in processor 330 can be an advice module 334, which arrives at advice based on outputs of detection module 332. Advice module 334 can include a Shock Advisory Algorithm, implement decision rules, and so on. The advice can be to shock, to not shock, to administer other forms of therapy, and so on. If the advice is to shock, some external defibrillator embodiments merely report that to the user, and prompt them to do it. Other embodiments further execute the advice, by administering the shock. If the advice is to administer CPR, defibrillator 300 may further issue prompts for it, and so on.

Processor 330 can include additional modules, such as module 336, for other functions. In addition, if other component 325 is indeed provided, it may be operated in part by processor 330, etc.

Defibrillator 300 optionally further includes a memory 338, which can work together with processor 330. Memory 338 may be implemented in any number of ways. Such ways include, by way of example and not of limitation, nonvolatile memories (NVM), read-only memories (ROM), random access memories (RAM), any combination of these, and so on. Memory 338, if provided, can include programs for processor 330, and so on. The programs can be operational for the inherent needs of processor 330, and can also include protocols and ways that decisions can be made by advice module 334. In addition, memory 338 can store prompts for user 380, etc. Moreover, memory 338 can store patient data.

Defibrillator 300 may also include a power source 340. To enable portability of defibrillator 300, power source 340 typically includes a battery. Such a battery is typically implemented as a battery pack, which can be rechargeable or not. Sometimes, a combination is used, of rechargeable and non-rechargeable battery packs. Other embodiments of power source 340 can include AC power override, for where AC power will be available, and so on. In some embodiments, power source 340 is controlled by processor 330.

Defibrillator 300 additionally includes an energy storage module 350. Module 350 is where some electrical energy is stored, when preparing it for sudden discharge to administer a shock. Module 350 can be charged from power source 340 to the right amount of energy, as controlled by processor 330. In typical implementations, module 350 includes one or more capacitors 352, and so on.

Defibrillator 300 moreover includes a discharge circuit 355. Circuit 355 can be controlled to permit the energy stored in module 350 to be discharged to nodes 314, 318, and thus also to defibrillation electrodes 304, 308. Circuit 355 can include one or more switches 357. Those can be made in a number of ways, such as by an H-bridge, and so on.

Defibrillator 300 further includes a user interface 370 for user 380. User interface 370 can be made in any number of ways. For example, interface 370 may include a screen, to display what is detected and measured, provide visual feedback to the rescuer for their resuscitation attempts, and so on. Interface 370 may also include a speaker, to issue voice prompts, etc. Interface 370 may additionally include various controls, such as pushbuttons, keyboards, and so on. In addition, discharge circuit 355 can be controlled by processor 330, or directly by user 380 via user interface 370, and so on.

Defibrillator 300 can optionally include other components. For example, a communication module 390 may be provided for communicating with other machines. Such communication can be performed wirelessly, or via wire, or by infrared communication, and so on. This way, data can be communicated, such as patient data, incident information, therapy attempted, CPR performance, and so on.

Defibrillator 300 may also include a utility light, such as illustrated by other component 325, which is structured to illuminate a certain point in a rescue environment or other areas around the defibrillator as needed by a rescuer or user. The utility light 325 may cast a beam of light at the certain point with a beam divergence angle of, for example, no more than 160 degrees so that the utility light can be directed at the certain point of interest.

Illuminating a particular area with a utility light 325 that is included with an external defibrillator 300 may include a variety of advantages over the prior art such as providing a rescuer 380 with the ability to illuminate certain points of a rescue environment without having to rely on a separate lighting device that can be forgotten or difficult to operate in a rescue situation. In addition, the utility light 325 of the defibrillator 300 may be controlled to provide communications to a rescuer 380 or other user.

Components sometimes similar to those of FIG. 3 are described in the remainder of this document. In some of the embodiments, similar components are named and numbered similarly as well.

Figure 4:
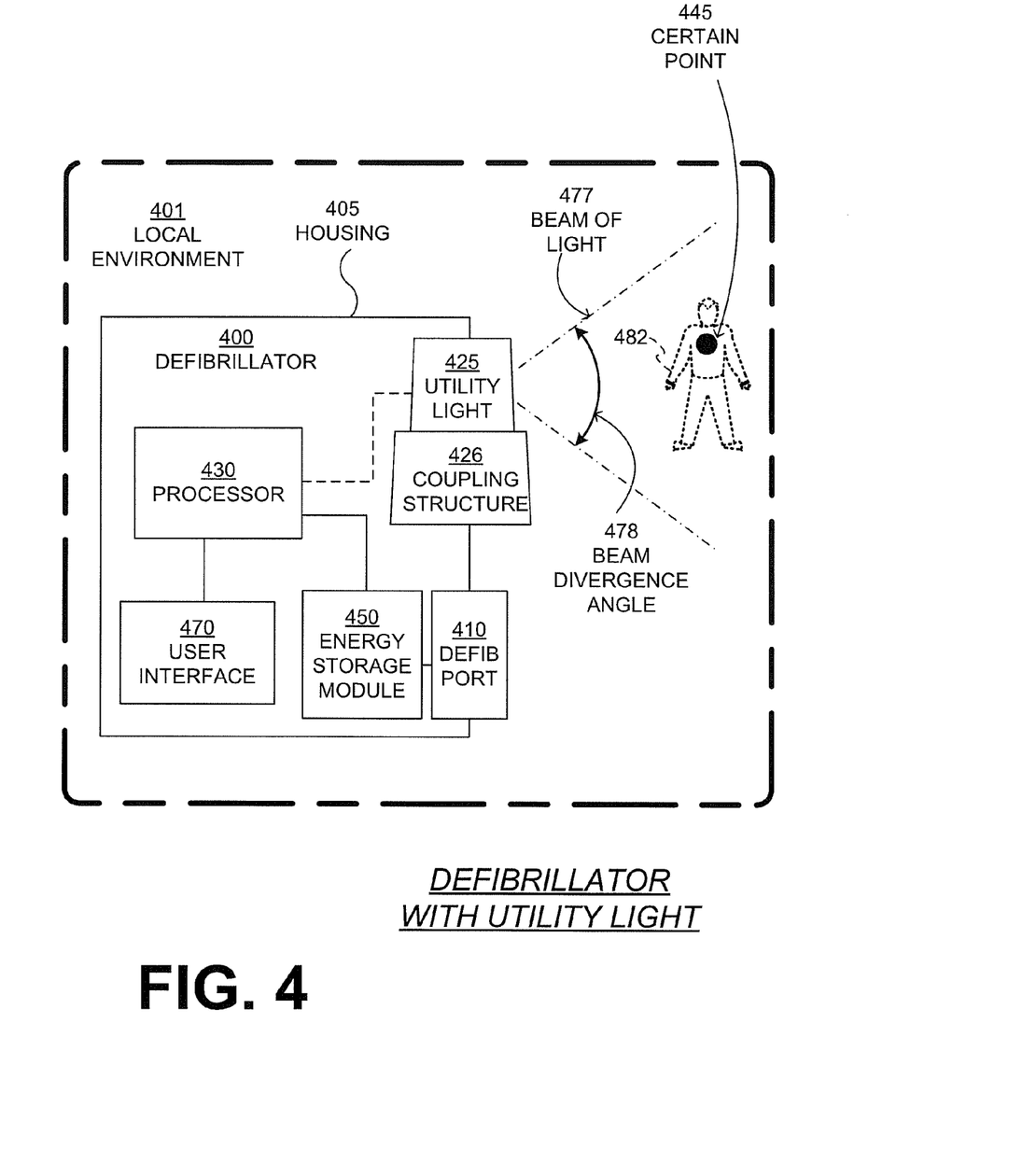
FIG. 4 is a diagram showing an external defibrillator with a utility light according to embodiments.

FIG. 4 is a diagram showing an external defibrillator 400 with a utility light 425 according to embodiments. The defibrillator 400 may be used in a local environment 401 with an ambient light level. The local environment 401 may be a rescue environment where a patient or person 482 is in need of medical assistance. Alternatively, the local environment 401 may be a pathway on the way to a rescue environment. For example, a rescuer may have to enter an unfamiliar darkened building and search for a person in need of medical assistance. Worse, they may have to climb an unlit stairway. Although these examples of a local environment 401 are provided to show example contexts in which the defibrillator 401 may be used, the local environment generally refers to the immediate area around the defibrillator.

The defibrillator 400 includes a housing 405 encompassing an energy storage module 450 used for storing an electrical charge. A defibrillation port 410 on the housing 405 is coupled to the energy storage module 450, and is used for guiding the stored electrical charge to a person 482 via at least one electrode 304, 308 (FIG. 3). The defibrillator 400 also includes a processor 430, which is used, among other things, for determining when to guide the electrical charge to the person 482. A user interface 470 having a screen showing indications by light is also included in the defibrillator 400. These components of the defibrillator 400 may be analogous to the similarly labeled components described above with reference to FIG. 3.

The housing 405 of the defibrillator 400 includes a light-coupling structure 426, which is used to matingly receive a utility light 425 distinct from the screen of the user interface 470. The utility light 425 is used for illuminating a certain point 445 of the local environment 401 by generating and casting a beam of light 477 at the certain point with a beam divergence angle 478 of no more than 160 degrees. The beam divergence meaning that, the beam's light intensity at 160/2=80 degrees in any direction from the centerline of the beam 477 is less than half of the beam's light intensity at the centerline.

The defibrillator 400 having a utility light 425 may be implemented in any number of ways. For example, the utility light 425 may include one or more light emitting diodes (LEDs), xenon bulbs, halogen bulbs, incandescent bulbs, or any other light sources capable of illuminating a desired area in a darkened local environment 401.

In addition to illuminating point 445 of local environment 401, the utility light 425 may perform various other functions. For example, in some embodiments, the processor 430 is configured to control the utility light to signal a rescuer by modulating the beam of light 477. Modulating the beam of the light 477 may attract the attention of the rescuer to an issue that needs attention. The issue can be specific to the light itself, such as an impending malfunction if it flickers in a certain way. Or it can be a general issue, in which case the light can attract attention to, say, a message being shown in a screen of user interface 470. For example, a measurement circuit 320 (FIG. 3) of the defibrillator 400 may detect that the electrical charges being guided to the person 482 are not working as anticipated due to an incorrect placement of the electrodes 304, 308 (FIG. 3) on the person. The modulating beam of light 477 from the utility light 425 may therefore be used to attract the attention of the rescuer. In addition, the beam of light 477 may be modulated in conjunction with signals from the user interface 470. Here, the modulated beam of light 477 may attract the attention of the rescuer while the user interface 470 may specify the type of issue that needs attention and instructions on how to resolve the issue.

In some embodiments, the user interface 470 is configured to display an operating mode of the utility light 425. For example, if the utility light 425 has adjustable brightness modes, the user interface 470 may indicate the current light level of the utility light 425. Additionally, the user interface 470 may be configured to allow a rescuer to adjust a characteristic of the beam of light 477. For example, the user interface 470 may include a button or switch to allow a user to operate the utility light 425, such as selecting a light level to use.

In some embodiments, the wavelength of the light beam 477 is adjustable. Adjusting the wavelength of the light beam may be used by a rescuer to visually emphasize different features of the local environment 401. For example, adjusting the wavelength of the light beam 477 from visible light wavelengths to infra-red light wavelengths may be used as an aid with night vision goggles, used to detect temperatures of objects in the local environment 401, used in spectroscopy, or in other uses. The utility light 425 may include a light source that is capable of varying the wavelength of the light beam 477, or multiple light sources may be included in the utility light. The adjustability of the light beam wavelength may be shown on and/or controlled at the user interface 470.

Figure 5:
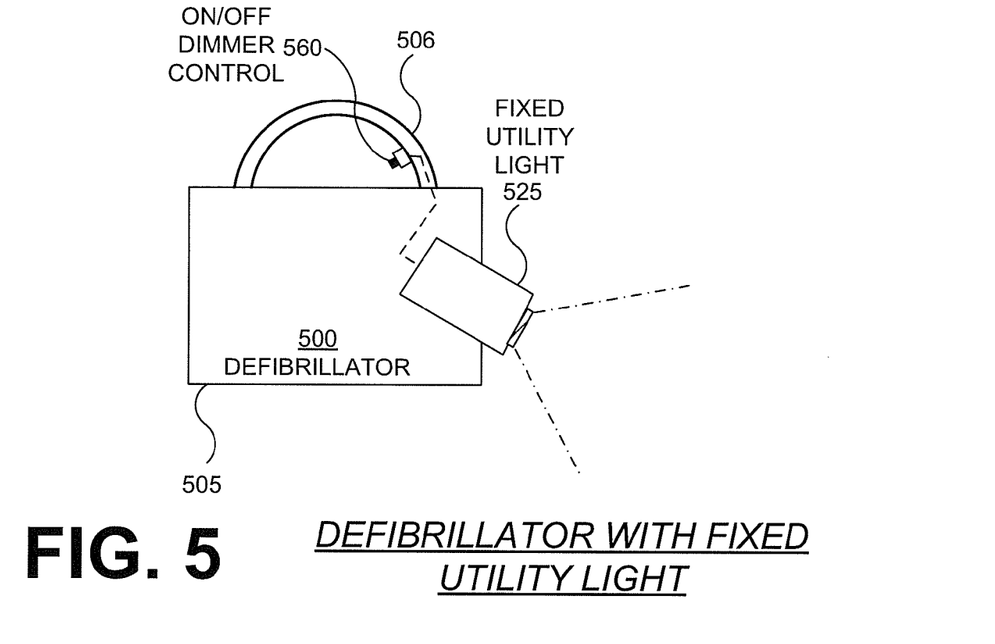
FIG. 5 is a diagram showing an external defibrillator with a fixed utility light according to embodiments.

FIG. 5 is a diagram showing an external defibrillator 500 with a fixed utility light 525 according to embodiments. Here, the utility light 525 is fixed to the housing 505 of the external defibrillator 500 via the light-coupling structure 426 (FIG. 4). This may be implemented in any number of ways. One way that the light-coupling structure 426 can be implemented in order to fix the utility light 525 to the housing 505 is by having the structure include a bolt attachment system where the fasteners are used to attach the utility light in a particular orientation to the defibrillator housing. This attachment system may be used to retrofit existing defibrillator units 500 with a utility light 525.

In some embodiments, the utility light 525 may be fixed so that it is oriented at a downward angle when the defibrillator is carried by its handle 506. This may help illuminate a darkened pathway in front of a rescuer when the defibrillator is being carried to a patient, or help search for a patient in a darkened area. The external defibrillator 500 may also include a switch 560 on the housing 505 to operate the utility light, where the switch is structured to be activated by a rescuer. As discussed above, the switch 560 may be located on, or be part of, a user interface 470 (FIG. 4). In other embodiments, the defibrillator 500 includes a carrying handle 506 in which the switch 560 is positioned adjacent to the handle and is controllable by a rescuer's carrying hand. These embodiments provide for one-handed operation of the utility light 525 while the defibrillator 500 is being carried. The switch 560 may allow a user to turn the utility light 525 on or off, as well as providing a selection for a light level or a dimmer control. For example, a button switch 560 may be pressed once to turn on to an initial light level, be pressed again for a second light level, be pressed a third time for a third light level, and be pressed again to be powered off.

Figure 6:
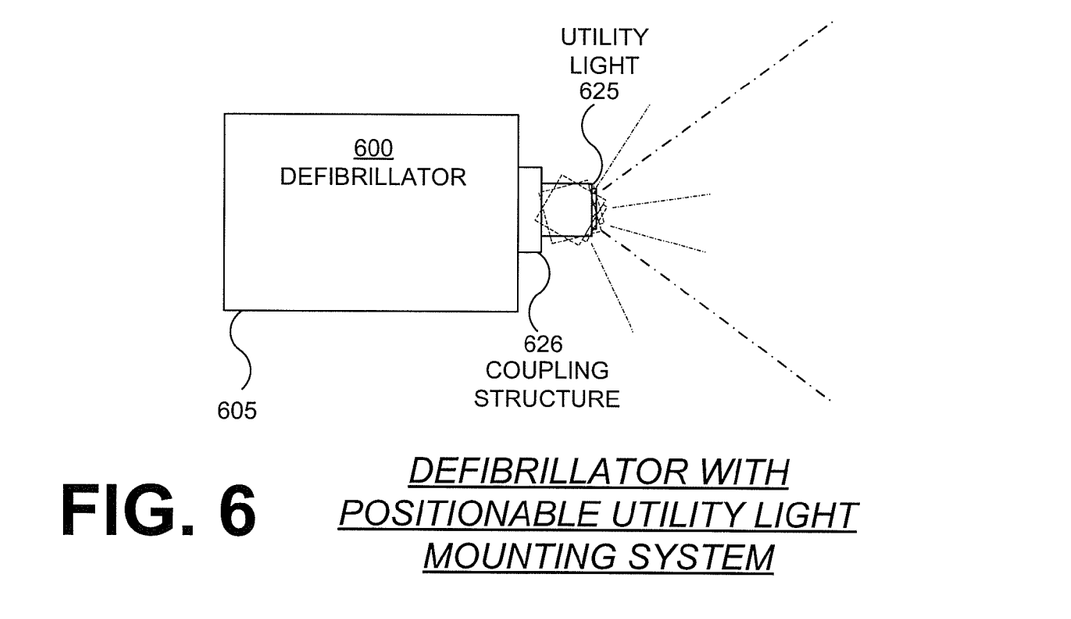
FIG. 6 is a diagram showing an external defibrillator with a positionable utility light mounting system according to embodiments.

FIG. 6 is a diagram showing an external defibrillator 600 with a positionable utility light mounting system 626 attached to a housing 605 of the defibrillator according to embodiments. As shown in FIG. 6, the coupling structure 626 is a positionable mounting system that allows an attached utility light 625 to be oriented in a variety of directions relative to the housing 605 of the defibrillator 600. As the dashed lines show in FIG. 6, the utility light 625 may be directed up and down relative to the housing 605. In addition, the coupling structure 626 may allow the utility light to be directing in a variety of horizontal directions relative to the housing 605. In some embodiments, the coupling structure 626 may include a ball-in-socket joint that allows the utility light to be moved with three degrees of freedom.

Figure 7:
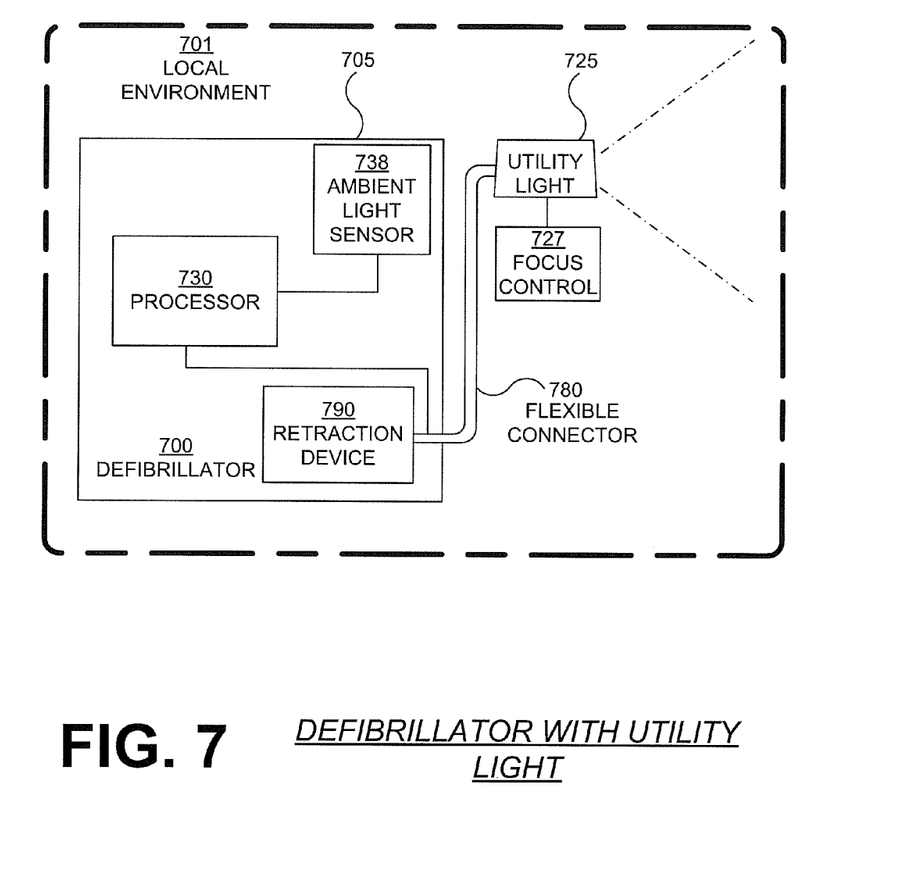
FIG. 7 is a diagram showing an external defibrillator with a retractable utility light according to embodiments.

FIG. 7 is a diagram showing an external defibrillator 700 with a retractable utility light 725 attached to a housing 705 according to embodiments. The defibrillator 700 has a light coupling structure that includes at least a partially flexible connector 780 for coupling the utility light 725 to the housing 705. In some embodiments, the flexible connector 780 is structured to retain its position after having been moved by a rescuer. Here, the rescuer may set the defibrillator 700 in a particular location, orient the utility light 725 to illuminate a desired area of the local environment 701, and then leave the defibrillator while the desired area remains illuminated. Hence, the rescuer can use both hands in administering medical attention or performing another action while having the utility light 725 illuminating a constant area in the local environment 701.

The external defibrillator 700 may also include a retraction device 790 structured to retract at least a portion of the flexible connector 780 into the housing 705. Here, when the utility light 725 is not in use, the flexible connector 780 can be stowed in the housing 705 so that the utility light does not become tangled with other equipment or get in the way when it is not needed.

The defibrillator 700 may also include a processor 730 and an ambient light sensor 738 configured to detect the ambient light level of the local environment 701. Additionally, the processor 730 may be configured to control the illumination of the utility light 725 according to the detected ambient light levels. Here, the processor 730 may increase the light level of the utility light 725 as the ambient light sensor 738 detects lower light levels in the local environment 701. Alternatively, the processor 730 may simply switch on the utility light 725 when the measured ambient light level drops below a predefined threshold.

In some embodiments, the utility light 725 includes at least one of a brightness control, a focusing control, or a beam divergence control (grouped together and labeled as focus control 727 in FIG. 7). These controls may allow a user or rescuer to adjust the beam of light from the utility light 725 from a broad spotlight to a narrow pin light. One way this may be accomplished is by having a rotatable bezel around the utility light 725 that moves a reflector dish longitudinally up or down relative to a bulb in the utility light.

Figure 8:
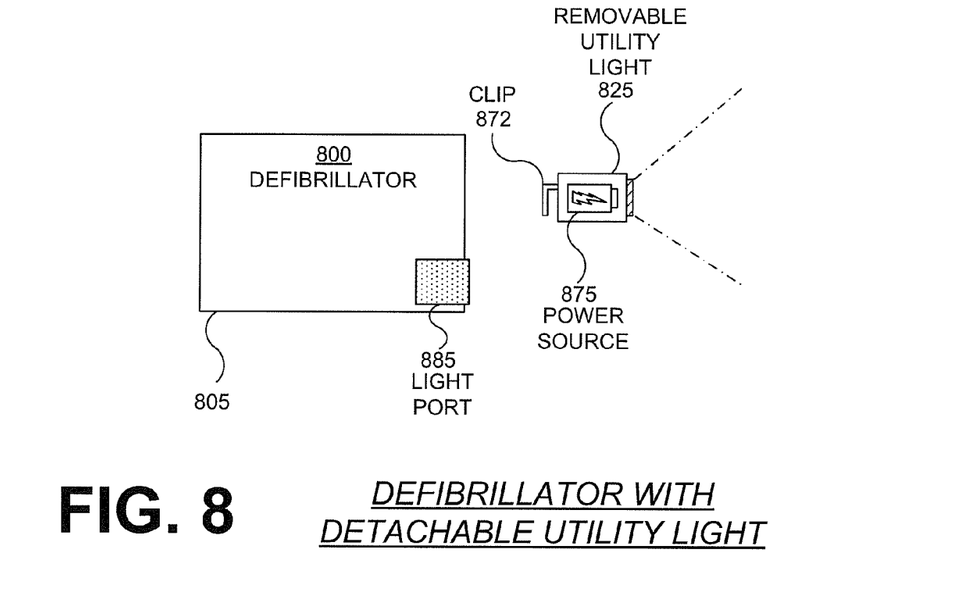
FIG. 8 is a diagram showing an external defibrillator with a removable utility light according to embodiments.

FIG. 8 is a diagram showing an external defibrillator 800 with a removable utility light 825 according to embodiments. Here, the utility light 825 is configured to be removable from a housing 805 of the defibrillator 800. The utility light 825 may include a dedicated power source 875 so that it is operable after having been removed from the housing 805 of the external defibrillator 800. This dedicated power source 875 may be automatically recharged from an internal power source 340 (FIG. 3) of the defibrillator 800 when the utility light 825 is connected to the housing 805 of the defibrillator. The internal power source 340 may power the screen of the user interface 470 (FIG. 4) and other components in the defibrillator as described above. In other embodiments, the internal power source 340 of the defibrillator 800 may power the removable utility light 825 as well via a wire or cord.

The light coupling structure of the defibrillator may include a dedicated port 885 for connecting the removable light 825. This dedicated port 885 may include an electrical connector that supplies power to the dedicated power source 875 from the internal power source 340 (FIG. 3) or another power source when the utility light 825 is connected to the port. In some embodiments, the port may include a well defined in the housing 805 for receiving therein a removable battery, where the utility light 825 is structured to be at least partially inserted in the well.

The removable utility light 825 may also include a clip 872 to attach the utility light to variety of objects. For example, the clip 872 may be structured to clip on to a hat or headband of a rescuer so that it can operate as a head lamp to illuminate objects in the direction the rescuer is facing.

Figure 9:
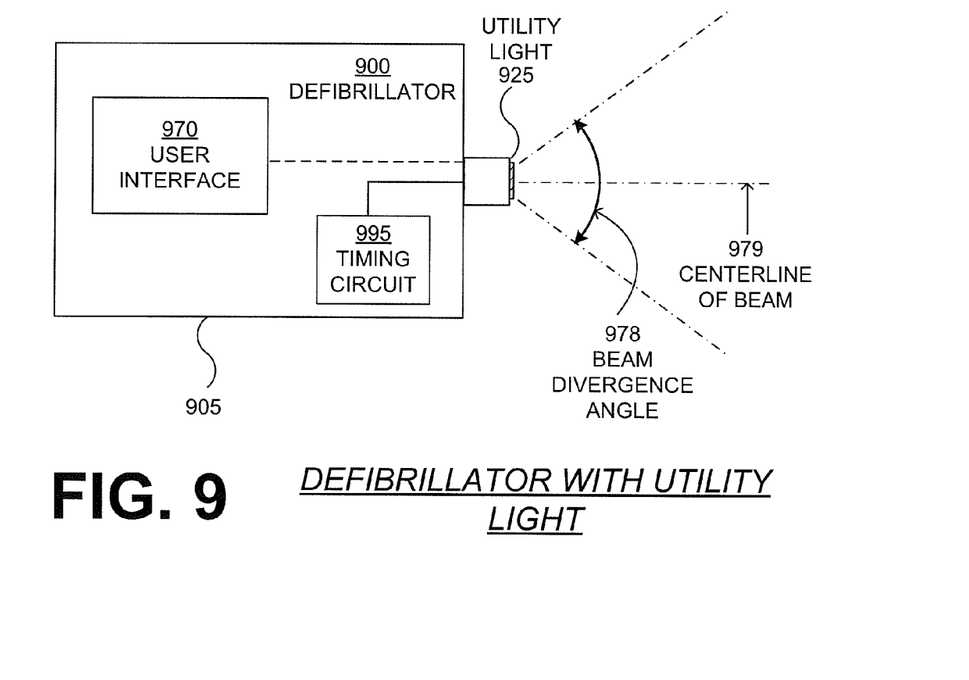
FIG. 9 is a diagram showing an external defibrillator with a user interface and utility light according to embodiments.

FIG. 9 is a diagram showing an external defibrillator 900 with a user interface 970 and utility light 925 positioned on a housing 905 of the defibrillator according to embodiments. Here, the external defibrillator 900 may also include a timing circuit 995 configured to deactivate the utility light 925 when a predetermined time limit of illumination is reached. The timing circuit 995 may prevent the utility light 925 from accidentally being activated and draining an internal power source 340 (FIG. 3) of the defibrillator 900. The user interface 970 may include a switch or feature to override the timing circuit 995 during use of the utility light 925 to prevent the light from being deactivated when it is needed. The defibrillator may also include a gyroscope or other motion sensor to detect when the defibrillator is in use to prevent the timing circuit 995 from deactivating the utility light 925.

Regardless of the particular features of embodiment 900, beam divergence angle 978 is also shown. Beam divergence angle 978 can be understood to be in two dimensions, or three. In addition, centerline 979 is also shown.

Figure 10:
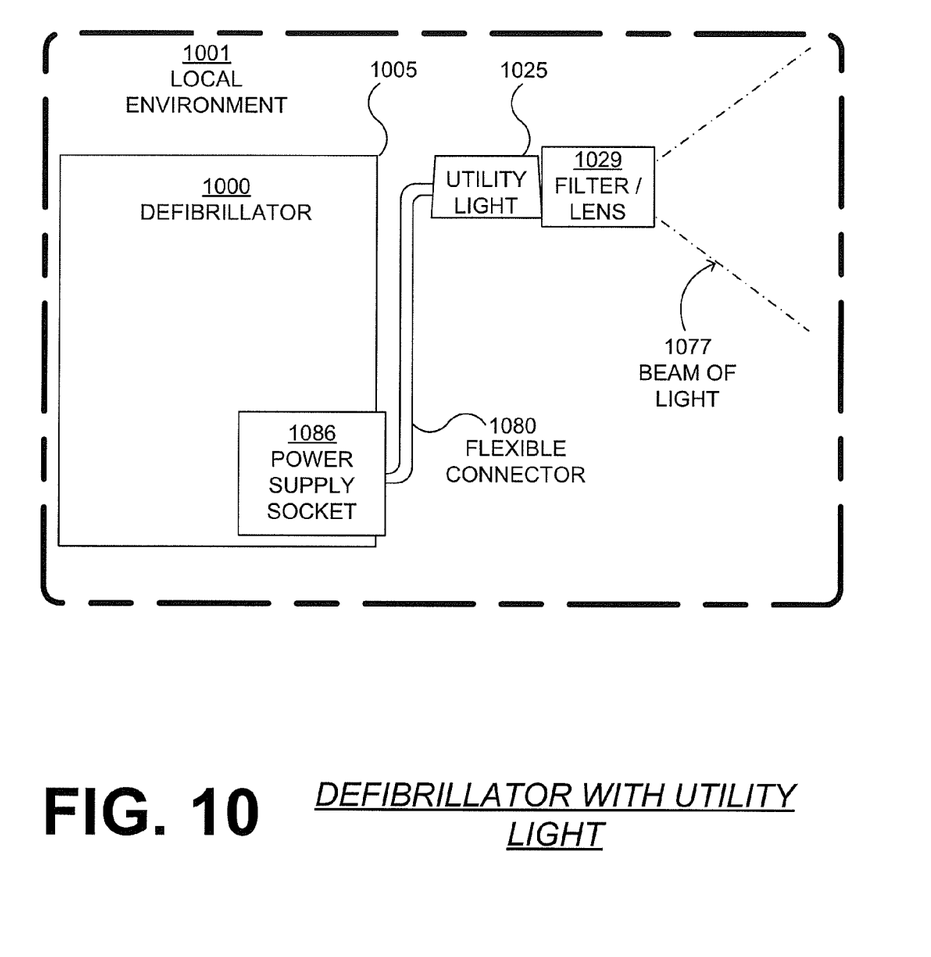
FIG. 10 is a diagram showing an external defibrillator with a utility light having a filter according to embodiments.

FIG. 10 is a diagram showing an external defibrillator 1000 with a utility light 1025 having a filter 1029 according to embodiments. Here, the defibrillator 1000 includes a power supply socket 1086 that is part of a light-coupling structure on a housing 1005 of the defibrillator 1000. The utility light 1025 is attached to a flexible connector 1080 that may be connected to the power supply socket 1086. Here, the utility light 1025 may be removable from the defibrillator 1000 when not in use. When needed, the utility light 1025 may be retrieved and the flexible connector 1080 may be inserted into the power supply socket 1086 to provide power to the utility light. The power supply socket 1086 may be configured to only provide power to a connected device.

The utility light 1025 may also have a filter or lens 1029 that is attached to it to modify a beam of light 1077 illuminating a local environment 1001. The filter 1029 may provide spectral filtering of a broadband light source in the utility light 1025. The filter 1029 may also adjust, modify, or limit the wavelength of the beam of light 1077.

Figure 11:
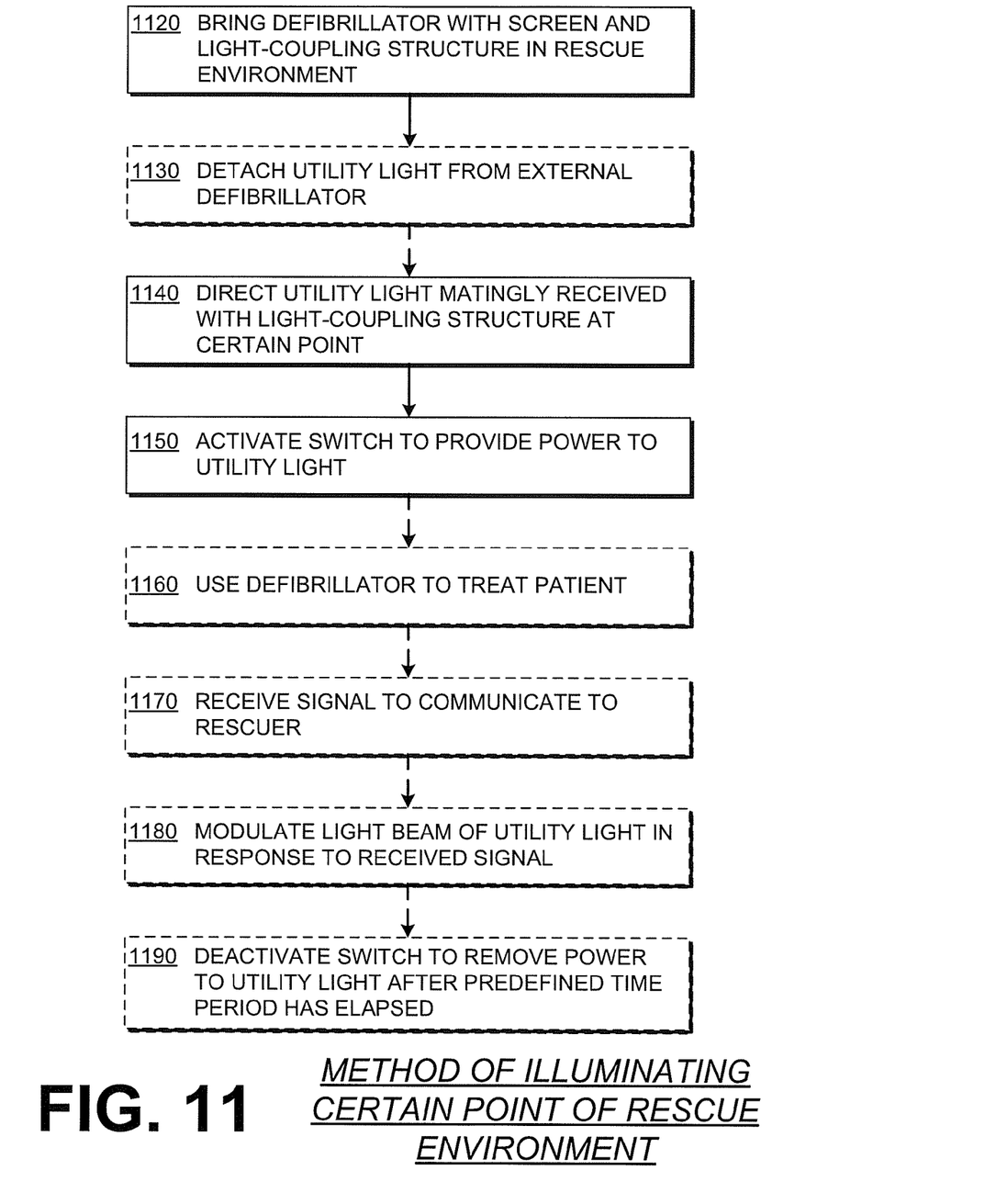
FIG. 11 is a flowchart for illustrating methods of illuminating a certain point of a rescue environment according to embodiments.

FIG. 11 is a flowchart for illustrating example methods according to embodiments. Although this flowchart illustrates a variety of operations in a particular order, these operations may be carried out in different orders to achieve similar results in other method embodiments. In particular, FIG. 11 illustrates a method of illuminating a certain point of a rescue environment according to embodiments. The method shown in this illustrated flow chart may be practiced, for example, by the defibrillator 400 shown in FIG. 4. According to an operation 1120, a defibrillator that stores an electrical charge is brought within a rescue environment. The defibrillator includes a screen showing indications by light and a light-coupling structure. The defibrillator also includes a utility light matingly received with the light-coupling structure that is distinct from the screen.

According to another operation 1150, a switch is activated to provide power to the utility light so as to generate a beam of light with a beam divergence angle of no more than 160 degrees. In some embodiments, this operation may include receiving a user input to activate the utility light, such as where this switch is activated by a rescuer or user. In other embodiments, this operation may include detecting an ambient light level of the rescue environment with an ambient light sensor, and receiving an input from the ambient light sensor when the detected ambient light level is below a predefined threshold. This operation may be completed, for example, to illuminate a pathway to the rescue environment with the utility light.

According to an optional operation 1130, the utility light may be detached from the external defibrillator. This operation 1130 may further include clipping or attaching the utility light to a headband, belt, hat, or other structure.

According to a next operation 1140, the utility light is directed so as to cast the beam towards a certain point of the environment. This operation 1140 may include manipulating a partially flexible connector of the light-coupling structure to position a beam generated by the utility light at the certain point. Alternatively, this operation 1140 may include moving the light relative to the housing of the defibrillator when the utility light is connected via a moveable coupling structure.

According to another optional operation 1160, if it is otherwise indicated by the defibrillator, the defibrillator may be used to treat a patient. According to another optional operation 1170, a signal may be received that is to be communicated to the rescuer. As discussed above, this signal may be an alert regarding the treatment of the patient, or another type of alert that the rescuer should be aware of. Here, a next optional operation 1180 modulates the light beam of the utility light in response to the signal received in operation 1170. The modulated light beam may be returned to a continuous light beam, or the light may be deactivated, by the rescuer by operating the user interface of the defibrillator. In yet another option operation 1190, the switch may be deactivated to remove power to the utility light when a predefined time period has elapsed.

In this description, numerous details have been set forth in order to provide a thorough understanding. In other instances, well-known features have not been described in detail in order to not obscure unnecessarily the description.

A person skilled in the art will be able to practice the present invention in view of this description, which is to be taken as a whole. The specific embodiments as disclosed and illustrated herein are not to be considered in a limiting sense. Indeed, it should be readily apparent to those skilled in the art that what is described herein may be modified in numerous ways. Such ways can include equivalents to what is described herein. In addition, the invention may be practiced in combination with other systems.

The following claims define certain combinations and subcombinations of elements, features, steps, and/or functions, which are regarded as novel and non-obvious. Additional claims for other combinations and subcombinations may be presented in this or a related document.

What is claimed is:

1. An external defibrillator for use in a local environment with an ambient light level, the external defibrillator comprising:
    a housing having a light-coupling structure;
    an energy storage module in the housing for storing an electrical charge;
    a defibrillation port for guiding, via at least one electrode coupled to the energy storage module, the stored electrical charge to a person;
    a processor for determining when to guide the electrical charge;
    a user interface that includes a screen showing indications by light;
    a utility light distinct from the screen for illuminating a certain point of the local environment, the utility light coupled to the housing by being received matingly with the light-coupling structure and structured to generate and cast a beam of light at the certain point with a beam divergence angle of no more than 160 degrees; and
    an ambient light sensor configured to detect the ambient light level of the local environment, and in which the processor is configured to control the illumination of the utility light according to the detected ambient light levels.

2. An external defibrillator for use in a local environment with an ambient light level, the external defibrillator comprising:
    a housing having a light-coupling structure;
    an energy storage module in the housing for storing an electrical charge;
    a defibrillation port for guiding, via at least one electrode coupled to the energy storage module, the stored electrical charge to a person;
    a processor for determining when to guide the electrical charge;
    a user interface that includes a screen showing indications by light; and
    a utility light distinct from the screen for illuminating a certain point of the local environment, the utility light coupled to the housing by being received matingly with the light-coupling structure and structured to generate and cast a beam of light at the certain point with a beam divergence angle of no more than 160 degrees, in which the utility light is configured to provide spectral filtering of a broadband light source.

3. An external defibrillator for use in a local environment with an ambient light level, the external defibrillator comprising:
    a housing having a light-coupling structure;
    an energy storage module in the housing for storing an electrical charge;
    a defibrillation port for guiding, via at least one electrode coupled to the energy storage module, the stored electrical charge to a person;
    a processor for determining when to guide the electrical charge;
    a user interface that includes a screen showing indications by light; and
    a utility light distinct from the screen for illuminating a certain point of the local environment, the utility light coupled to the housing by being received matingly with the light-coupling structure and structured to generate and cast a beam of light at the certain point with a beam divergence angle of no more than 160 degrees, in which the wavelength of the light illuminating the certain point of the local environment is adjustable.

4. An external defibrillator for use in a local environment with an ambient light level, the external defibrillator comprising:
a housing having a light-coupling structure;
an energy storage module in the housing for storing an electrical charge;
a defibrillation port for guiding, via at least one electrode coupled to the energy storage module, the stored electrical charge to a person;
a processor for determining when to guide the electrical charge;
a user interface that includes a screen showing indications by light; and
a utility light distinct from the screen for illuminating a certain point of the local environment, the utility light coupled to the housing by being received matingly with the light-coupling structure and structured to generate and cast a beam of light at the certain point with a beam divergence angle of no more than 160 degrees, in which the utility light includes at least one of a brightness control, a focusing control, or a beam divergence control.

5. The external defibrillator of claim 4, in which
the housing defines a well for receiving therein a removable battery, and
the utility light is structured to be at least partially inserted in the well.

6. An external defibrillator for use in a local environment with an ambient light level, the external defibrillator comprising:
a housing having a light-coupling structure;
an energy storage module in the housing for storing an electrical charge;
a defibrillation port for guiding, via at least one electrode coupled to the energy storage module, the stored electrical charge to a person;
a processor for determining when to guide the electrical charge;
a user interface that includes a screen showing indications by light; and
a utility light distinct from the screen for illuminating a certain point of the local environment, the utility light coupled to the housing by being received matingly with the light-coupling structure and structured to generate and cast a beam of light at the certain point with a beam divergence angle of no more than 160 degrees, in which the user interface is configured to allow a rescuer to adjust a characteristic of the beam.

7. The external defibrillator of claim 6, in which the utility light is fixed to the housing via the light coupling structure.

8. The external defibrillator of claim 7, in which the light-coupling structure allows a direction of the beam to change relative to the housing.

9. The external defibrillator of claim 6, further comprising a switch on the housing to operate the utility light, the switch structured to be activated by the rescuer.

10. The external defibrillator of claim 9, further comprising a carrying handle in which the switch is positioned adjacent to handle and is controllable by the rescuer's carrying hand.

11. An external defibrillator for use in a local environment with an ambient light level, the external defibrillator comprising:
a housing having a light-coupling structure;
an energy storage module in the housing for storing an electrical charge;
a defibrillation port for guiding, via at least one electrode coupled to the energy storage module, the stored electrical charge to a person;
a processor for determining when to guide the electrical charge;
a user interface that includes a screen showing indications by light; and
a utility light distinct from the screen for illuminating a certain point of the local environment, the utility light coupled to the housing by being received matingly with the light-coupling structure and structured to generate and cast a beam of light at the certain point with a beam divergence angle of no more than 160 degrees, in which the user interface is configured to display an operating mode of the utility light.

12. An external defibrillator for use in a local environment with an ambient light level, the external defibrillator comprising:
a housing having a light-coupling structure;
an energy storage module in the housing for storing an electrical charge;
a defibrillation port for guiding, via at least one electrode coupled to the energy storage module, the stored electrical charge to a person;
a processor for determining when to guide the electrical charge;
a user interface that includes a screen showing indications by light;
a utility light distinct from the screen for illuminating a certain point of the local environment, the utility light coupled to the housing by being received matingly with the light-coupling structure and structured to generate and cast a beam of light at the certain point with a beam divergence angle of no more than 160 degrees; and
a timing circuit configured to deactivate the utility light when a predetermined time limit of illumination is reached.

13. An external defibrillator for use in a local environment with an ambient light level, the external defibrillator comprising:
a housing having a light-coupling structure;
an energy storage module in the housing for storing an electrical charge;
a defibrillation port for guiding, via at least one electrode coupled to the energy storage module, the stored electrical charge to a person;
a processor for determining when to guide the electrical charge;
a user interface that includes a screen showing indications by light; and
a utility light distinct from the screen for illuminating a certain point of the local environment, the utility light coupled to the housing by being received matingly with the light-coupling structure and structured to generate and cast a beam of light at the certain point with a beam divergence angle of no more than 160 degrees, in which the processor is configured to control the utility light to signal a rescuer by modulating the beam of light.

14. The external defibrillator of claim 13, in which the light-coupling structure includes at least a partially flexible connector for coupling the utility light to the housing.

15. The external defibrillator of claim 14, further comprising a retraction device structured to retract at least a portion of the flexible connector into the housing.

16. The external defibrillator of claim 14, in which the flexible connector is structured to retain its position after having been moved by a rescuer.

17. The external defibrillator of claim 13, in which the utility light is removable from the housing.

18. The external defibrillator of claim 17, in which the light-coupling structure includes a dedicated port for connecting the removable utility light.

19. The external defibrillator of claim 18, in which the removable utility light includes a dedicated power source and is operable after having been removed from the housing of the external defibrillator.

20. The external defibrillator of claim 18, further comprising:
a power source for powering the screen, and
in which the removable utility light is powered from the power source.

21. The external defibrillator of claim 13, in which the beam of light is modulated in conjunction with signals from the user interface.

22. A method comprising:
bringing within a rescue environment a defibrillator that stores an electrical charge, includes a screen showing indications by light, and also includes a light-coupling structure, the defibrillator having a utility light matingly received with the light-coupling structure and distinct from the screen;
activating a switch to provide power to the utility light so as to generate a beam of light with a beam divergence angle of no more than 160 degrees, in which activating the switch includes:
detecting an ambient light level of the rescue environment with an ambient light sensor; and
receiving an input from the ambient light sensor when the detected ambient light level is below a predefined threshold;
directing the utility light so as to cast the beam towards a certain point of the environment; and
if it is otherwise indicated by the defibrillator, using the defibrillator to deliver the charge to treat a patient in the environment.

23. A method comprising:
bringing within a rescue environment a defibrillator that stores an electrical charge, includes a screen showing indications by light, and also includes a light-coupling structure, the defibrillator having a utility light matingly received with the light-coupling structure and distinct from the screen;
activating a switch to provide power to the utility light so as to generate a beam of light with a beam divergence angle of no more than 160 degrees;
directing the utility light so as to cast the beam towards a certain point of the environment;
if it is otherwise indicated by the defibrillator, using the defibrillator to deliver the charge to treat a patient in the environment; and
automatically deactivating the switch to remove power to the utility light when a predefined time period has elapsed.

24. A method further comprising:
bringing within a rescue environment a defibrillator that stores an electrical charge, includes a screen showing indications by light, and also includes a light-coupling structure, the defibrillator having a utility light matingly received with the light-coupling structure and distinct from the screen;
activating a switch to provide power to the utility light so as to generate a beam of light with a beam divergence angle of no more than 160 degrees;
directing the utility light so as to cast the beam towards a certain point of the environment;
if it is otherwise indicated by the defibrillator, using the defibrillator to deliver the charge to treat a patient in the environment;
receiving a signal to be communicated to a rescuer; and
modulating a beam of light generated by the utility light in response to the received signal.

25. A method comprising:
bringing within a rescue environment a defibrillator that stores an electrical charge, includes a screen showing indications by light, and also includes a light-coupling structure, the defibrillator having a utility light matingly received with the light-coupling structure and distinct from the screen;
activating a switch to provide power to the utility light so as to generate a beam of light with a beam divergence angle of no more than 160 degrees;
directing the utility light so as to cast the beam towards a certain point of the environment;
if it is otherwise indicated by the defibrillator, using the defibrillator to deliver the charge to treat a patient in the environment; and
illuminating a pathway to the rescue environment with the utility light.

26. The method of claim 25, in which directing the utility light towards the certain point includes manipulating a partially flexible connector of the light-coupling structure to position a beam generated by the utility light at the certain point.

27. The method of claim 25, further comprising detaching the utility light from the external defibrillator.

28. The method of claim 25, in which activating the switch includes receiving a user input to activate the utility light.

29. The method of claim 25, further comprising receiving a removable battery in a well defined by the defibrillator.

30. The method of claim 29, further comprising at least partially inserting the utility light in the well.

* * * * *